United States Patent [19]

Gonsalves et al.

[11] Patent Number: 5,514,570
[45] Date of Patent: May 7, 1996

[54] SQUASH MOSAIC VIRUS GENES AND PLANTS TRANSFORMED THEREWITH

[75] Inventors: Dennis Gonsalves; Shengzhi Pang, both of Geneva, N.Y.; John Hu, Honolulu, Hi.

[73] Assignee: Cornell Research Foundation, Ithaca, N.Y.

[21] Appl. No.: 363,560

[22] Filed: Dec. 21, 1994

Related U.S. Application Data

[63] Continuation of Ser. No. 85,250, Jun. 30, 1993, abandoned, which is a continuation of Ser. No. 750,180, Aug. 27, 1991, abandoned.

[51] Int. Cl.$^6$ .............................. A01H 1/04; C07H 17/00; C12N 5/14; C12N 15/00
[52] U.S. Cl. ................................. 435/172.3; 435/240.4; 536/23.1; 536/23.72; 800/205; 800/DIG. 18
[58] Field of Search ........................... 800/205, DIG. 21, 800/DIG. 18; 536/23.1, 23.72; 435/172.3, 252.3, 240.4, 320.1

[56] References Cited

FOREIGN PATENT DOCUMENTS

| | | | |
|---|---|---|---|
| 0223452 | 5/1987 | European Pat. Off. | C12N 15/00 |
| 0262972 | 6/1988 | European Pat. Off. | A01H 1/00 |
| WO86/05516 | 9/1986 | WIPO | C12P 21/00 |

OTHER PUBLICATIONS

Nejidat et al. (1990) Physiolgra Plantarum 80: 662–668.
van Wezenbeek et al. (1983) EMBO J. 2:941–46.
Hiebert et al. (1981) Virology 113:630–636.
Cuozzo et al. (1988) Bio/Technology 6:549–57.
Hu, J. S. et al., "Molecular Cloning of Complementary DNA Copies of Squash Mosaic Virus," Proceedings of the First Conference of the Association of Chinese Agriculture Students and Scholars, p. 112 [abstract] (1989).
Hu, J. S. et al. "Molecular Cloning of Complementary DNA of Squash Mosaci Virus," Phytopathology 80(1):120 Abstract (1990).
Hu, J. S. and D. Gonsalves, "Cloning and Sequencing of Squash Mosaic Virus Coat Protein Genes," Abstracts of VIIIth International Congress of Virology, Berlin, West Germany, p. 456 [poster that was presented on Aug. 31, 1990] (1990).
Beachy, R. N. et al. "Coat Protein–Mediated Resistance Against Virus Infection," Annu. Rev. Phytopathology 28:451–74 (1990).
Bruening, G., "Comovirus Group," CMI/AAB Descriptions of Plant Viruses—No. 199, (Aug. 1978).
Campbell, R. N., "Squash Mosaic Virus," CMI/AAB Descriptions of Plant Viruses—No. 43 (Jun. 1971).
Goldbach, R. and A. vanKammen, "Structure, Replication, and Expression of the Bipartite Genome of Cowpea Mosaic Virus", Molecular Plant Virology 2:83–120 (1985).
Hiebert E. and D. E. Purcifull, "Mapping of the Two Coat Protein Genes on the Middle RNA Component of Squash Mosaic Virus (Comovirus Group)," Virology 113:630–36 (1981).
Nelson, M. R. and H. K. Knuhtsen, "Squash Mosaci Virus Variabiltiy: Review and Serological Comparisons of Six Biotypes," Phytopathology 63:920–26 (1973).
Shanks, M. et al., "The Primary Structure of Red Clover Mottle Virus Middle Component RNA," Virology 155:697–706 (1986).
vanWezenbeek, P. et al., "Primary Structure and Gene Organization of the Middle–Component RNA of Cowpea Mosaic Virus," The EMBO J. 2:941–46 (1983).
Cuozzo, M. et al.., "Viral Protection in Transgenic Tobacco Plants Expressing the Cucumber Mosaic Virus Coat Protein or its Antisense RNA," Bio/Technology 6:549–57 (1988).
Hemenway, C. et al., "Analysis of the Mechanism of Protection in Transgenic Plants Expressing the Potato Virus X Coat Protein or its Antisense RNA," The EMBO J. 7(5):1273–80 (1988).
Hill, K. K. et al., "The Development of Virus–Resistant Alfalfa, *Medicago Sativa L.*," Bio/Technology 9:373–77 (1991).
Hoekema, A. et al., "The Genetic Engineering of Two Commerical Potato Cultivars for Resistance to Potato Virus X," Bio/Technology 7:273–78 (1989).
Kaniewski, W. et al., "Field Resistance of Transgenic Russet Burbank Potato to Effects of Infection by Potato Virus X and Potato Virus Y," Bio/Technology 8:750–53 (1990).
Kawchuk, L. M. et al., "Resistance in Transgenic Potato Expressing the Potato Leafroll Virus Coat Protein Gene," Molecular Plant–Microbe Interactions 3(5):301–07 (1990).
Lawson, C. et al., "Engineering Resistance to Mixed Virus Infection in a Commercial Potato Cultivar: Resistance to Potato Virus X and Potato Virus Y in Transgenic Russet Burbank," Bio/Technology 8:127–34 (1990).
Ling, K. et al., "Protection Against Detrimental Effects of Potyvirus Infection in Transgenic Tobacco Plants Expressing the Papaya Ringspot Virus Coat Protein," Bio/Technology 9:752–58 (1991).
Loesch–Fries, L. S. et al., "Expression of Alfalfa Mosaic Virus RNA 4 in Transgenic Plants Confers Virus Resistance," The EMBO J. 6(7):1845–51 (1987).
MacKenzie, D. J. et al., "Genetically Engineered Resistance to Potato Virus S in Potato Cultivar Russet Burbank," Molecular Plant–Microbe Interactions 4(1):95–102 (1991).
Fang, G. and R. Grumet, "*Agrobacterium Tumefaiens* Mediated Transformation and Regeneration of Muskmelon Plants," Plant Cell Report 9:160–64 (1990).
Abel, P. P. et al., "Delay of Disease Development in Transgenic Plants that Express the Tobacco Mosaic Virus Coat Protein," Science 232:738–43 (1986).

(List continued on next page.)

*Primary Examiner*—Douglas W. Robinson
*Assistant Examiner*—Elizabeth F. McElwain
*Attorney, Agent, or Firm*—Fitzpatrick, Cella, Harper & Scinto

[57] ABSTRACT

Squash mosaic virus coat protein genes are disclosed. Expression vectors containing squash mosaic virus coat protein genes are disclosed. Transgenic plants that contain squash mosaic virus coat protein genes and that are resistant to infection by squash mosaic virus are disclosed.

8 Claims, No Drawings

OTHER PUBLICATIONS

Quemada, H. D. et al., "Expression of Coat Protein Gene from Cucumber Mosaic Virus Strain C in Tobacco: Protection Against Infections by CMV Strains Transmitted Mechanically or by Aphids," Phytopathology 81(7):794–802 (1991).

J. L. Slightom, "Custom Polymerase–Chain–Reaction Engineering of a Plant Expression Vector," Gene 100:251–55 (1991).

Stark, D. M. and R. N. Beachy, "Protection Against Potyvirus Infection in Transgenic Plants: Evidence for Broad Spectrum Resistance," Bio/Technology 7:1257–62 (1989).

Tumer, N. E. et al., "Expression of Alfalfa Mosaci Virus Coat Protein Gene Confers Cross–Protection in Transgenic Tobacco and Tomato Plants," The EMBO J. 6:1181–88 (1987).

vanDun, C. M. P. et al., "Transgenic Tobacco Expressing Tobacco Streak Virus or Mutated Alfalfa Mosaic Virus Coat Protein Does Not Cross–Protect Against Alfalfa Mosaic Virus Infection," Virology 164:388–89 (1988).

vanDun, C. M. P. and J. F. Bol. "Transgenic Tobacco Plants Accumulating Tobacco Rattle Virus Coat Protein Resist Infection with Tobacco Rattle Virus and Pea Early Browning Virus," Virology 167:649–52 (1988).

SQUASH MOSAIC VIRUS GENES AND PLANTS TRANSFORMED THEREWITH

The present application is a continuation of Ser. No. 08/085,250, filed Jun. 30, 1993, now abandoned, which is a continuation of Ser. No. 08/750,180, filed Aug. 27, 1991, now abandoned.

FIELD OF INVENTION

The present invention relates to squash mosaic virus coat protein genes. The present invention also relates to transgenic plants that contain squash mosaic virus coat protein genes. Such transgenic plants are resistant to infection by squash mosaic virus.

BACKGROUND OF THE INVENTION

Squash mosaic virus (SqMV) is a member of comovirus group, with isometric virus particles about 30 mm in diameter. Virus capsid is composed of two distinct polypeptides with molecular weights of 22 and 42 kilodaltons. A viral genome of members of comovirus group consists of two single-stranded, positive-sense RNA molecules identified as middle-component RNA (M-RNA) and bottom-component RNA (B-RNA) of ca. 4200 and 6000 nucleotides, respectively. Both M-RNA and B-RNA are polyadenylated at the 3'-ends and have a genomic-linked protein (VPg) at the 5'-termini. The RNAs are translated into polyproteins from which the functional proteins are derived by proteolytic cleavages.

SqMV induces diseases on squash and melons, and is transmitted by beetles and through seeds. Control of the virus is normally through the use of virus-free seeds and insecticides for the control of beetles. While these methods can achieve some level of success in reducing the level of infection in a crop, they are time consuming and relatively expensive. However, no SqMV-resistant genes have been identified in squash or melons which would render plants carrying such genes resistant to SqMV infection. It is desirable to have strains of squash and melon plants which are resistant to SqMV infection. According to the present invention, SqMV infection in melons and squash is controlled by coat protein-mediated protection.

Expression of the coat protein genes from tobacco mosaic virus, alfalfa mosaic virus, cucumber mosaic virus, watermelon II mosaic virus, papaya ringspot virus, zucchini yellow mosaic virus and potato virus X in transgenic plants has resulted in plants which are resistant to infection by the respective virus. In order to produce such transgenic plants, the coat protein gene must be isolated and inserted into the genome of the plant. Furthermore, the coat protein gene must contain all the genetic control sequences necessary for the expression of the gene after it has been incorporated into the plant genome.

One distinction between SqMV and the other viruses listed above is that SqMV virus capsid is composed of two different types of coat proteins whereas the other viruses have a single type of coat protein. It is necessary to determine if the expression of one or both coat protein genes is required for coat protein-mediated protection. This necessitates identification of the coat protein genes, engineering the genes into plant expression and transformation vectors, transforming plants to express the coat protein genes singly or doubly, and testing plants for resistance to infection.

In the present invention, the nucleotide sequences of the coat protein genes for SqMV have been determined and the genes have been inserted into expression vectors to supply them with the necessary genetic regulatory sequences so that the genes can be expressed when incorporated into a plant genome. Plant cells are transformed with the vector construct and the plant cells are induced to regenerate. The resulting plants express the coat protein genes that they contain. The transgenic plants according to the present invention are resistant to infection by the SqMV.

INFORMATION DISCLOSURE

European patent application EP 0 223 452 describes plants that are resistant to viral diseases and methods for producing them. The process described comprises the steps of transforming a plant with a DNA insert comprising a promoter, a DNA sequence derived from the virus, and a poly(A) addition sequence.

PCT patent application PCT/US86/00514 refers generally to a method of conferring resistance to a parasite to a host of the parasite.

Hu, J. S., L'Hostis, B., Kearney, C., Provvidenti, R, and D. Gonsalves, (1989) Molecular cloning of complementary DNA copies of squash mosaic virus, Proceedings of the First Conference of the Association of Chinese Agricultural Students and Scholars p. 112 (abstract), describe production of cDNA clones. No nucleic acid sequence or engineering data was known at that time.

Hu, J. S., L'Hostis, B., Kearney, C., and D. Gonsalves, (1989) Molecular cloning of complementary DNA copies of squash mosaic virus, Phytopathology 79:120 (abstract), describe production of cDNA clones. No nucleic acid sequence or engineering data was known at that time.

Hu, J. S. and D. Gonsalves, (1990) Cloning and sequencing of squash mosaic virus coat protein genes, Abstracts of VIIIth International Congress of Virology, Berlin, West Germany, p. 456, relate to a poster that was presented on Aug. 31, 1990, at the VIIIth International Congress of Virology, Berlin, West Germany. The sequence of the cDNA, which was believed to contain the coat protein genes of squash mosaic virus, was presented in the poster. The polyprotein cleavage sites had not been determined at that time.

Beachy, R. N. et al., (1990) Coat protein-mediated resistance against virus infection, Ann. Review of Phytopathol. 28:451–474, summarize the literature on coat protein-mediated protection up to 1989–90.

G. Bruening, (1978) Comovirus group, CMI/AAB Descriptions of Plant Virus No. 199, describes the properties of the Comovirus group; the group to which squash mosaic virus belongs.

R. N. Campbell, (1971) Squash mosaic virus, CMI/AAB Descriptions of Plant Virus No. 43, describes the biology and physical properties of squash mosaic virus.

Goldbach, R. and A. Karomen, (1985) Structure, replication and expression of the bipartite genome of cowpea mosaic virus, "Molecular Plant Virology" (J. W. Davies, ed.), 2:83–120. CRC Press, Boca Raton, Fla., summarize the genome organization of the comovirus group.

Hiebert, E. and D. E. Purcifull, (1981) Mapping of the two coat protein genes on the middle RNA component of squash mosaic virus (comovirus group), Virology 113:630–636 disclose that in vitro translation of the middle RNA of squash mosaic virus produces the two coat proteins of squash mosaic virus.

Nelson, M. R. and H. K. Kunhtsen, (1973) Squash mosaic virus variability: review and serological comparisons of six biotypes, Phytopathology 63:920–926, describe various isolates of squash mosaic virus.

Shanks, M. et al., (1986) The primary structure of red clover mottle virus middle component RNA, Virology 155:697–706, disclose the nucleic acid sequence of the middle RNA which presumably contains the coat protein of red clover mottle virus, which belongs to the comovirus group.

vanWezenbeek, P. et al., (1983) Primary structure and gene organization of the middle component RNA of cowpea mosaic virus, EMBO J. 2:941–946, disclose the nucleic acid sequence of middle RNA of cowpea mosaic virus.

Cuozzo, M. et al., (1988) Viral protection in transgenic tobacco plants expressing the cucumber mosaic virus coat protein or its antisense RNA, Bio/Technology 6:549–557, disclose that transgenic tobacco expressing coat protein gene of cucumber mosaic virus is resistant to cucumber mosaic virus infection.

Hemenway, C. et al., (1988) Analysis of the mechanism of protection in transgenic plants expressing the potato virus X coat protein or its antisense RNA, EMBO J. 7:1273–1280, disclose that transgenic potato expressing coat protein gene of potato virus X are resistant to potato virus X infection.

Hill, K. K. et al., (1991) The development of virus-resistant alfalfa, *Medicago sativa* L, Biotechnology 9:373–377, disclose that alfalfa expressing the coat protein gene of alfalfa mosaic virus are resistant to alfalfa mosaic virus infection.

Hoekema, A. et al., (1989) The genetic engineering of two commercial potato cultivars for resistance to potato virus X, Bio/Technology 7:273–278, disclose that transgenic potato expressing coat protein gene of potato virus X are resistant to potato virus X infection.

Kaniewski, W. K. et al., (1990) Field resistance of transgenic Russet Burbank potato to effects of infection by potato virus X and potato virus Y, Bio/Technology 8:750–754, disclose that transgenic potato expressing both coat protein genes of potato virus X and potato virus Y are resistant to infection by these viruses.

Kawchuk, L. M. et al., (1990), Resistance in transgenic potato expressing the potato leaf roll virus coat protein gene, Mol. Plant-Microbe Interactions 3:301–307, disclose that potato expressing coat protein gene of potato leaf roll virus are resistant to infection by that virus.

Lawson, C. et al., (1990) Engineering resistance to mixed virus infection in a commercial potato cultivar: Resistance to potato virus X and potato virus Y in transgenic russet burbank, Bio/Technology 8:127–134, disclose that transgenic potato expressing both coat protein genes of potato virus X and potato virus Y are resistant to infection by these viruses.

Ling, K. et al., (1991), Protection against detrimental effects of polyvirus infections in transgenic tobacco plants expressing the papaya ringspot virus coat protein gene, Bio/Technology 9:752–758, disclose that tobacco expressing the coat protein gene of papaya ringspot virus show resistance to infection by tobacco etch virus, pepper mottle virus, and potato virus Y.

Loesch-Fries, L. S. et al., (1987) Expression of alfalfa mosaic virus RNA4 in transgenic plants confers virus resistance, EMBO J. 6:1845–1851, disclose that transgenic plants expressing coat protein gene of alfalfa mosaic virus are resistant to infection by alfalfa mosaic virus.

Mackenzie, D. J. et at., (1991) Genetically engineered resistance to potato virus S in potato cultivar russet burbank, Mol. Plant-Microbe Interactions 4:95–102, disclose resistance to infection of potato virus S.

Fang, G. and R. Grumet, (1990) *Agrobacterium tumefaciens* mediated transformation and regeneration of muskmelon plants, Plant Cell Reports, 9:160–164, disclose procedure for obtaining transgenic melons expressing the NPTII and GUS genes.

Powell-Abel, P. et al., (1986) Delay of disease development in transgenic plants that express the tobacco mosaic virus coat protein gene, Science 232:738–743, disclose that transgenic plants expressing the coat protein gene of tobacco mosaic virus are resistant to infection by tobacco mosaic virus.

Quemada, H. D. et al., (1991) CMV-C coat protein expressed in tobacco: protection against infections by CMV strains transmitted mechanically or by aphids, Phytopathology 81:794–802, disclose that tobacco expressing the coat protein gene of the C isolate of the cucumber mosaic virus show resistance to infection by cucumber mosaic virus by mechanical and aphid inoculation.

J. L. Slightom, (1991) Custom PCR engineering of a plant expression vector, Gene 100:251–255, discloses that polymerase chain reaction using specific primers is a fast and convenient way to precisely engineer coat protein genes into plant expression vectors.

Stark, D. M. and R. N. Beachy, (1989) Protection against polyvirus infection in transgenic plants: Evidence for Broad spectrum resistance, Bio/Technology 7:1257–1262, disclose that transgenic tobacco expressing coat protein gene of soybean mosaic virus are resistant to infection by tobacco etch virus and potato virus Y.

Tumer, N. E. et al., (1987) Expression of alfalfa mosaic virus coat protein gene confers cross-protection in transgenic tobacco and tomato plants, EMBO J. 6:1181–1188, disclose that transgenic plants expressing the coat protein gene of alfalfa mosaic virus are resistant to infection by alfalfa mosaic virus.

VanDun, C. M. P. and J. F. Bol, (1988) Transgenic tobacco plants accumulating tobacco rattle virus coat protein resist infection with tobacco rattle virus and pea early browning virus, Virology 167:649–652, disclose that transgenic plants expressing tobacco rattle virus coat protein gene show resistance to infection by tobacco rattle virus coat protein gene show resistance to infection by tobacco rattle virus and by pea early browning virus.

VanDun, C. M. P. et al., (1988) Transgenic tobacco expressing tobacco streak virus or mutated alfalfa mosaic virus coat protein does not cross-protect against alfalfa mosaic virus infection, Virology 164:383–389, disclose that tobacco expressing the coat protein gene of tobacco streak virus or a mutated coat protein gene of alfalfa mosaic virus are not resistant to alfalfa mosaic virus infection.

SUMMARY OF THE INVENTION

The present invention relates to the coat protein genes of Squash Mosaic Virus (SqMV). The present invention relates to recombinant DNA molecules which encode SqMV coat proteins. The present invention relates to recombinant DNA molecules that comprise SqMV coat protein genes operably linked to genetic regulatory sequences necessary for gene expression. Furthermore, the present invention relates to transgenic plants which comprise recombinant DNA molecules that encode SqMV coat proteins and that are operably linked to genetic regulatory sequences necessary for gene expression. In addition, the present invention relates to a process of producing transgenic plants which have increased resistance to SqMV infection.

DETAILED DESCRIPTION OF THE INVENTION

The recombinant DNA methods employed in practicing the present invention are standard procedures, well known to those skilled in the art, and described in detail in, for example, European Patent Application Publication Number 223452, published Nov. 29, 1986, which is incorporated herein by reference. Enzymes are obtained from commercial sources and are used according to the vendor's recommendations or other variations known in the art. General references containing such standard techniques include the following: R. Wu, ed. (1979) Methods in Enzymology, Vol. 68; J. H. Miller (1972) Experiments in Molecular Genetics; T. Maniatis et al. (1982) Molecular Cloning: A Laboratory Manual; D. M. Glover, ed. (1985) DNA Cloning Vol. II; H. G. Polites and K. R. Marotti (1987) "A step-wise protocol for cDNA synthesis". Biotechniques 4:514–520; S. B. Gelvin and R. A. Schilperoort, eds. Introduction, Expression, and Analysis of Gene Products in Plants, all of which are incorporated by reference.

For the purposes of the present disclosure the following definitions apply.

"Promoter" means a promoter which is functional in the host plant.

"Initiation region" includes the initiation codon and nucleotides flanking the initiation codon.

"Operably linked" refers to the linking of nucleotide regions encoding specific genetic information such that the nucleotide regions are contiguous, the functionality of the region is preserved and will perform its function relative the other regions as part of a functional unit.

"AT rich 5' untranslated region" is a nucleotide sequence composed of at least 60% adeninc or thymine nucleotides.

"Untranslated flanking region" refers to nucleotide sequences which are 3' of the termination codon and end at the poly(A) addition signal. These sequences enhance production of the peptide encoded by the upstream gene.

"Vector" is a vehicle by means of which DNA fragments can be introduced into host organisms.

"Expression vector" is a vehicle by means of which DNA fragments that contain sufficient genetic information and can, therefore, be expressed by the host, can be introduced into host organisms.

To practice the present invention, coat protein genes of SqMV are isolated from the viral genome and inserted into a vector containing the genetic regulatory sequences necessary to express the inserted gene. When the expression vector/insert construct is assembled, it is used to transform plant cells which are then used to transgenic regenerate plants which are capable of expressing the viral genes in the expression vector/insert constructs. When the genes are expressed in the plant, resistance to viral infection is conferred thereby.

The nucleotide sequence and the deduced amino acid sequences of both of the coat protein genes of squash mosaic virus are given in Seq ID 1. The 22K protein is encoded by nucleotides 1819 to 2370 of Seq ID 1. The 42K is encoded by nucleotides 700 to 1818 of Seq ID 1. The N-terminus of the 22 Kd protein is a serine residue at nucleotide number 1819. This N-terminus was determined by direct amino acid sequence analysis of the N-terminus of the 22 Kd protein of squash mosaic virus. The amino acid sequence at the N-terminus of the 42 Kd protein could not be determined because the protein is N-terminally blocked. Therefore, the putative N-terminus of the 42K coat protein was predicted based on the comparison of the amino acid sequence of SqMV with those of cowpea mosaic virus (CPMV) and red clover mottle virus (RCMV), and on the calculated molecular weight of the deduced protein. Based on these data, the cleavage site for SqMV was predicted to be Q/N, while that reported for CPMV is Q/M, and for RCMV is Q/T. The molecular weight (43K) of this deduced protein is very close to the molecular weight (42K) of the protein determined in sodium dodecylsulfate polyacrylamide gel electrophoresis.

The length of the 3' untranslated region of SqMV (124 bp) is similar to that of CPMV (181 bp) but much shorter than the untranslated region of RCMV (261 bp). The M-RNAs of SqMV, CPMV, and RCMV use different termination codons (UAG for SqMV, UAA for CPMV, UGA for RCMV). Using computer-aided analyses (GCG program package) no significant degree of sequence identity shared among SqMV, polyviruses and animal viruses at either the nucleotide or amino acid sequence level was found.

Four oligonucleotide primers were designed, based on the cDNA sequence of SqMV that was obtained and the predicted cleavage sites of the polyprotein, for the amplification of the SqMV coat protein genes from the cDNA clone (pSM10). The primers are as follows:

Seq ID 3 -JLS91-16: TCTTGAGGATCCATGG-GAACTGGGAAAGAAGCCAC which is complementary to the 3' untranslated region of polyprotein gene of M RNA;

Seq ID 4 -JLS91-17: TACTFATCTAGAACCATG-GAGCTAGATCTTGCGCAACT based on the 5'terminus of SqMV 42K (and 64K) protein gene;

Seq ID 5 -JLS91-18: TACAGTGGATCCATGGTTC-TACTGCCCAGAAATTCCTAGTA complementary to the 3' end of SqMV 42K protein gene;

Seq ID 6 -JLS91-21: TACAGTTCTAGAAGAACCATG-GTACAGCAGCTTGG based on the 5' end of SqMV 22K protein gene.

The NcoI restriction enzyme site was incorporated into these primers to facilitate further cloning. The ATG codons contained in NcoI site of 5' primers Seq ID 3 and Seq ID 5 (JLS91-17 and 21) were designed for the translation initiation codons of all the coat protein genes, and the TGA in the 3' primer Seq ID 4 (JLS91-18) of the 42K coat protein served as the stop codon of this protein, since all the coat proteins of SqMV are produced by the post translational cleavage of polyprotein.

The nucleotide sequences which encode the coat proteins for SqMV were inserted into expression vectors that contain the necessary genetic regulatory sequences for expression of an inserted gene in plants. The coat protein genes were inserted such that those regulatory sequences are functional so that the genes can be expressed when incorporated into a plant genome. The plant expression vector plasmid pUC18CPEXP, described in the published PCT international patent application PCT/US089/03095, incorporated herein by reference, is useful as the preferred embodiment for constructing a SqMV insert in an expression cassette. Other embodiments of useful expression cassettes suitable for insertion of SqMV coat protein gene sequences are described in PCT/US089/03095. The coat protein gene is engineered to contain a plant expressible promoter, a translation initiation codon (ATG) and a plant functional poly(A) addition signal (AATAAA) 3' of its translation termination codon. In the present invention, the coat protein is inserted into a vector which contains a cloning site for insertion 3' of the initiation codon and 5' of the poly(A) signal. The promoter is 5' of the initiation codon such that when a structural gene is inserted at the cloning site, a functional unit is formed in which the inserted gene is expressed under the control of the various genetic regulatory sequences.

In one embodiment of the present invention, additional genetic regulatory sequences are provided. As described above, an expression vector must contain a promoter, an initiation codon and a poly(A) addition signal. In order to get a higher level of expression, untranslated regions 5' and 3' to the inserted genes are provided. Furthermore, certain sequences flanking the initiation codon optimize expression. The promoter used is one that is chosen for high level expression.

A 5' untranslated region which results in higher level expression of an inserted gene is provided downstream from the promoter and upstream from the initiation codon. This region contains at least 60% of the sequence a Adenine and Thymine. There is a statistical bias for expression when such an AT rich region is located between the promoter and initiation codon. This preference is utilized in the preferred embodiment of the present invention by inclusion of an AT rich 5' untranslated region intermediate of the promoter and initiation codon.

One embodiment of the present invention also contains specific nucleotide sequence flanking the initiation codon. This preferred sequence, termed Kozak's element, is AAXXATGG wherein X represents any of the four nucleotides. The presence of the initiation codon following Kozak's rule results in higher level expression when used in an expression vector. In the preferred embodiment of the present invention, the small subunit from the SS RUBISCO contains an initiation codon in which Kozak's element is used.

Furthermore, one embodiment of the present invention contains a 3' untranslated region downstream from the cloning site where the coat protein gene is inserted and upstream from the poly(A) addition signal. The sequence of this 3' untranslated region results in a statistical bias for protein production. The sequence promotes high level expression. The poly(A) addition signal is found directly downstream from the 3' untranslated region and can be derived from the same source. In the preferred embodiment of the present invention, the 3' untranslated region and poly(A) addition signal are derived from CaMV 35S gene or the phaseolin seed storage protein gene.

The poly(A) addition signal from CaMV, nopaline synthase, octopine synthase, bean storage protein, and SS RUBISCO genes are also suitable for this construction. Several promoters which function in plants are available, but the best promoters are the constitutive promoter from cauliflower mosaic virus (CaMV, a plant DNA virus) and the small subunit of ribulose bis-phosphate carboxylase-oxygenase (SS RUBISCO) gene.

Using methods well known to those skilled in the art, plant cells are transformed with the vector construct and the plant cells are induced to regenerate. The resulting plants contain the coat protein genes and produce the coat protein. The production of the protein confers upon the plant an increased resistance to infection by the virus from which the coat protein gene was derived.

Four sets of inserts are used to construct vectors. Vectors are constructed that contain individual 22K, 42K and 64K inserts as well as a vector that contains both 22K and 42K inserts, each within separate expression cassettes and inserted into the same vector in tandem. Transformations are performed using single vectors and transgenic squash and melon plants are then generated which express the genes encoded by the inserts. A double transformation using vectors that contain 22K only and 42K only are also performed and transgenic squash and melon plants are generated from such transformed cells.

Squash or melon cells with vectors that contain the various coat protein gene inserts are generated using either *Agrobacterium tumefaciens* or microprojectile transformation. Transformed cells are selected and regenerated in kanamycin medium, and roots are induced on root-inducing medium. Rooted transformants are transferred to soil and grown under greenhouse conditions. The transgenic plants are challenged with SqMV to screen the transgenic clones which are resistant to the virus.

DESCRIPTION OF THE PREFERRED
EMBODIMENTS

EXAMPLE 1

Preparation of DNA Encoding SqMV Coat Proteins

An isolate of SqMV group I (melon strain) was obtained from infected melon seeds and typed as the melon strain by biological comparisons with the type strain. Virus propagation, purification and RNA extraction were done as described (Hieben and Purcifull, 1981 Virology 113:630–636). First strand complementary DNA (cDNA) of SqMV M-RNA was synthesized by reverse transcriptase using oligo dTP primers. The double-stranded cDNA was fractionated by sucrose gradient centrifugation, methylated to prevent internals cuts by EcoRI, and EcoRI compatible linkers were attached to both termini. After digestion with EcoRI, cDNAs were cloned into the EcoRI site of pUC18, which had been dephosphorylated. *E. coli* DH5 competent cells were transformed and selected as described by Hanahan (1986) J. Miol. Biol 166:557–562. Small- and large-scale plasmid preparations were made by the alkaline method. Plasmid and restriction digests were analyzed by electrophoresis in 1% agarose. Colony hybridization and Southern blot hybridization were performed with cDNA probes from SqMV M-RNA, using Genescreen Plus membrane, following the protocols provided by the vendor (DuPont).

The genes encoding SqMV coat proteins are isolated as cDNA molecules. The nucleotide sequences of the cDNAs for both coat proteins are reported in Sequence ID 1. The 22K coat protein is encoded by nucleotides 1819 to 2370 of Seq ID 1. The 42K coat protein is encoded by nucleotides 700 to 1818 of Seq ID 1. Using the sequences disclosed in Sequence ID 1, SqMV coat protein genes may be synthesized chemically by methods well known in the art. Alternatively, the information in Sequence ID I may be used to synthesize oligonucleotides which can be used as probes to screen a cDNA library.

SqMV coat proteins were extracted with the LiCl method and partially digested with V 8 proteinase. Fragments of the digested coat proteins were purified by high pressure liquid chromatography (HPLC), and sequenced at the Biotechnology Center, Cornell University. Using the determined amino acid sequence, oligonucleotides (27 bases long) having a degeneracy of 32 to cover all possible codons were synthesized at the Biotechnology Center, Cornell University and used as a mixture in hybridization experiments to identify cDNA clones that contain the coat protein genes.

A few hundred colonies with viral inserts were identified by colony hybridization and seventy-five of them were selected for further analysis. Inserts were confirmed to be virus specific by Southern blot hybridization. Restriction enzyme mapping of six clones, ranging in size from 0.7 to 3.2 kb, showed that the clones had the same 3'-terminal region. In hybridization tests, the oligonucleotide probe, produced based on coat protein fragment sequence, reacted with clones 1.5 kb or longer, but not with smaller ones.

Two strategies were used to sequence the cDNA clones. First, the extreme 350–400 bases from both ends of five clones ranging in size from 0.7 to 2.5 kb were sequenced. DNA sequencing was done from both ends of double-stranded plasmids by the dideoxynucleotide chain-termination method with T 7 DNA polymerase, following protocols provided by the vendor (Pharmacia). The second strategy used the nested deletion approach. A series of exonuclease III digestion deletions were generated from a clone (pSM10) by termination of reaction at 2 min intervals. The remaining single-stranded protrusions were prepared with an "acid phenol" procedure and sequenced. Samples were subjected to electrophoresis on 100 cm gels, as described by Slightom, et al. (1987) J. Biol. Chem. 262:7472–7483. Sequence data was compiled and analyzed using the GCG computer program (available from GCG, Inc., Madison, Wisc.).

Restriction enzyme mapping had shown that these five cDNA clones had the same 3'-end region, and thus formed a "natural nest". Sequence analysis identified overlaps between the sequences of adjacent clones. The identification of a poly (A) tract in all the clones indicated that the entire 3'-untranslated region had been cloned. In the second sequencing strategy, one clone (2.5 kb, pSM10) was sequenced by the nested deletion approach. Since coat protein genes of other comoviruses are located at the extreme 3' end of the M-RNA, pSM10 was predicted to be long enough to include the two coat protein genes. This approach also served to verify the sequences obtained from the first strategy. Sequence analysis of overlapping clones from the two strategies provided a 2497 bp sequence of the 3'-half of SqMV M-RNA, along with the deduced amino acid sequence of a single long open reading frame (ORF) The ORF had a coding capacity of 830 amino acid residues. The ORF encoded the 26 amino acid sequence peptide of the 42K coat protein which was used to prepare oligonucleotides for identifying cDNA clones containing SqMV coat protein sequences. There is an untranslated region (127 bp) and a poly (A) tail at the 3'-end. The total sequence obtained was 2497 bp, plus a poly (A) tail, represents about half of the complete SqMV M-RNA, with an expected length of 4.2 kb.

Plasmid pSM10 containing the full length of two coat protein genes was used in polymerase chain reactions to amplify and construct the coat protein genes with each pair (1 μl each) of the primers, according to manufacturer's instructions (Perkin Elmer Cetus). A typical cycle was 1 Min at 92° C. (denature), 1 min at 50 C (anneal), and 2.5 min at 72 C (polymerize). The samples were directly loaded and separated on 1.2% agarose gel. The separated coat protein gene fragments were extracted from agarose gel, ethanol-precipitated and dissolved in 20 μl of water.

The gel-isolated coat protein gene fragments were digested with the restriction enzyme NcoI, passed through G-50 spin column, and directly cloned into NcoI-digested plant expression vector pUC18CPEXP in both orientations. The plant expression vector plasmid pUC18CPEXP is described in the published PCT international patent application PCT/US089/03095 which is incorporated herein by reference. The resulting plant expression vector plasmids were identified and designated as pUC 18CPEXP-22K, pUC 18CPEXP-42K and pUC 18CPEXP-64K, respectively, in the correct orientation relative to the cauliflower mosaic 35S promoter, and as pUC18CPEXP- 22K(-), pUC18CPEXP-42K(-) or pUC18CPEXP-64K(-) in the reverse orientation.

The expression cassettes containing the coat protein genes were excised from each of the respective plant expression vector plasmids by digestion with HindIII, and subsequently ligated into plant transformation vector pBIN19 (Clonetech Laboratories, Inc.) that had been cut with the same enzyme. The resulting vectors, designated pBIN19-22K, pBIN19-42K, and pBIN19-64K respectively, are used for microprojectile bombardment transformation of squash or melons or transferred into Agrobacterium strain LBA4404 for Agrobacterium-mediated transformation.

EXAMPLE 2

Microprojectile Transfer into Plant Tissues

Recently an alternative approach for the transfer and integration of DNA into a plant genome has been developed. The apparatus and method are described in U.S. Pat. No. 4,945,050 which is incorporated herein by reference. This technique relies on the use of microprojectiles on which the DNA (plasmid form) is attached. These microprojectiles are accelerated to high velocities and their momentum is used to penetrate plant cell walls and membranes. After penetration into a plant cell the attached DNA leaches off the microprojectile and is transferred to the nucleus where DNA repair enzymes integrate the "free" DNA into the plant genome. In its present form the process is entirely random, but plant tissues which have been successfully transformed by the plasmid DNA (or part of it) can be identified and cultured to homogeneity by the use of selectable marker genes (such as the bacterial neomycin phosphotransferase II gene, NPTII), or reporter genes (such as the bacterial beta-glucuronidase gene, Gus). The use of this process for the transfer of plasmids containing SqMV cDNA in expression cassettes can be accomplished after the addition of either plant expressible NPTII or Gus genes or both.

The expression cassettes containing the coat protein genes are excised from each of the respective plant expression vector plasmids pUC18CPEXP-22K, pUC18CPEXP-42K and pUC18CPEXP-64K by digestion with HindIII, and subsequently ligated into plant transformation vector pBIN19 (Clonetech Laboratories, Inc.) that had been cut with the same enzyme. The resulting vectors are designated pBIN19-22K, pBIN1942K, and pBIN19-64K respectively. Additionally, the expression cassettes containing the coat protein genes are excised from each of the respective plant expression vector plasmids pUC18CPEXP-22K and pUC18CPEXP-42K by digestion with HindIII, and subsequently ligated in tandem into single plant transformation vector pBIN19 (Clonetech Laboratories, Inc.) that had been cut with the HindIII. This plasmid is referred to as pBIN19-22K/42K. Vectors pBIN19-22K, pBIN19-42K, pBIN19-64K and pBIN19-22K/42K respectively are individually used for microprojectile bombardment transformation of squash or melons. In addition, pBIN19-22K and pBIN19-42K are used together in a microprojectile bombardment transformation. Thus, a total of 5 transformations are performed.

EXAMPLE 3

Construction of Binary Vectors

Three binary plasmid vectors were constructed for insertion of expression cassette/coat protein gene inserts; binary plasmid vectors pGA482GG, pPRBoriGN, and PPRBN. The binary plasmids are used to transfer the expression cassette/coat protein gene inserts into plant genomes. The parent binary plasmid was pGA482 (Pharmacia KLB Biotechnology, Piscataway, N.J.). This binary vector contains the T-DNA border sequences from pTiT37, the selectable marker gene Nos-NPT II (which contains the plant-expressible nopaline gene promoter fused to the bacterial NPT II gene obtained from Tn5), a multiple cloning region, and the cohesive ends of phage lambda. The first vector made was pGA482GG. A second identifiable marker, the plant-expressible beta-glucuronidase (GUS) gene was inserted into the BglII site of the multiple cloning region of pGA482. In addition, to aid in the transfer of this binary plasmid into C58Z707 or A208.35, the bacteria-derived gentamicin-(3)-N-acetyl-transferase gene was cloned into a SalI site outside of the T-DNA region, adjacent to the left border (BL).

The second vector made was pPRBoriGN. The plasmid pPRBoriGN is a derivative of the plasmid pGA482 with the following alterations:

1. A bacterial selectable marker, gentamicin resistance, was inserted adjacent to the right border ($B_R$), but outside the T-DNA region.
2. The Nos-nptII gene was excised and the multiple cloning site (MCS) is regenerated adjacent to $B_R$, just inside the T-DNA region.
3. A plant-expressible GUS cassette (see pGA482GG) was inserted within the T-DNA region adjacent to the pBR322 origin of replication (ori).
4. A plant-expressible nptII cassette produced by insertion of the nptII coding region into the expression cassette of the E. coli plasmid pDH51 was inserted inside the T-DNA region adjacent to the left border ($B_L$). This nptII gene is driven by the cauliflower mosaic virus (CaMV) 35S promoter and terminated by the CaMV polyadenylation signal.

The third vector made was pPRBN. The plasmid pPRBN is a derivative of pPRBoriGN with the following alterations:

1. The region of pPRBoriGN from the beginning of the GUS coding sequence to $B_L$ was deleted. Therefore, the GUS gene and 35S/nptII cassette were removed as a unit.
2. This region was replaced by a fragment consisting of the 35S/nptII cassette only. The net result of these steps was the removal of the GUS gene plus a short region of pBR322 homology, leaving the plant expressible NPTII gene adjacent to $B_L$.

EXAMPLE 4

Construction of Binary Vectors that Contain SqMV Coat Protein Genes in Expression Cassettes The plant expression cassette containing cDNA encoding SqMV coat protein as described in Example 1 is transferred into a suitable micro T-DNA vector which contains the necessary Agrobacterium T-DNA transfer signals for transfer from an Agrobacterium and integration into a plant genome, and a wide host-range origin of replication (for replication in Agrobacterium). Plasmids pUC18CPEXP-22K, pUC18CPEXP42K and pUC18CPEXP-64K respectively are digested with HindIII and the resulting insert fragment containing the plant-expressible cassette including the cDNA is removed and ligated into the HindIII site of the multiple cloning site of one of the modified Agrobacterium-derived binary vectors described in Example 3. IN addition to insertion of a single construct into a vector, expression cassettes containing 22K and 42K are inserted in tandem in each of the three binary plasmids. Accordingly, twelve vectors are constructed:

1) pGA482GG/CPEXP-22K
2) pGA482GG/CPEXP42K
3) pGA482GG/CPEXP-64K
4) pGA482GG/CPEXP-22K/42K
5) pPRBoriGN/CPEXP-22K
6) pPRBoriGN/CPEXP-42K
7) pPRBoriGN/CPEXP-64K
8) pPRBoriGN/CPEXP-22K/42K
9) pPRBN/CPEXP-22K
10) pPRBN/CPEXP42K
11) pPRBN/CPEXP-64K
12) pPRBN/CPEXP-22K/42 K The vectors are transferred into plant cells which can then be regenerated into transgenic plants. This transfer can be accomplished using the standard methods for T-DNA transfers which are known to those skilled in the art, or this transfer can be accomplished using the methods described in a U.S. patent application Ser. No. 07/135,655, filed on Dec. 21, 1987, entitled "Agrobacterium Mediated Transformation of Germinating Plant Seeds" and incorporated herein by reference.

The typical gene transfer experiment involves the insertion of expression cassettes containing coat protein genes, followed by their cloning into the vectors pGA482GG, pPRBoriGN or pPRBN to generate the vectors listed above. The vectors are transferred into *Agrobacterium tumefaciens* strains C58Z707 or A208.35. Transformed C58Z707 or A208.35 bacteria are plated on TY agar plates containing 50 µg/ml kanamycin and 40 µg/ml gentamicin, and those containing the binary plasmid are selected because of their ability to grow more rapidly on this medium. The presence of the binary plasmid is confirmed by restriction enzyme digestion and Southern blot analysis. The C58Z707 or A208.35 bacteria containing the desired plasmids are then used to infect cantaloupe or squash tissues.

We claim:

1. A recombinant DNA molecule comprising a nucleotide sequence selected from the group consisting of nucleotides 1819 to 2370 of Seq ID 1 and nucleotides 700 to 1818 of Seq ID 1.

2. A recombinant DNA molecule according to claim 1 wherein said recombinant DNA molecule has the nucleotide sequence of nucleotides 1819 to 2370 of Seq ID 1.

3. A recombinant DNA molecule according to claim 1 wherein said recombinant DNA molecule has the nucleotide sequence of nucleotides 700 to 1818 of Seq ID 1.

4. A transgenic *Cucur bitaceae* plant comprising a recombinant DNA molecule according to claim 1.

5. A transgenic plant according to claim 4 wherein said recombinant DNA molecule has the nucleotide sequence of nucleotides 1819 to 2370 of Seq ID 1.

6. A transgenic plant according to claim 4 wherein said recombinant DNA molecule has the nucleotide sequence of nucleotides 700 to 1818 of Seq ID 1.

7. A transgenic plant according to claim 5 wherein said recombinant DNA molecule further comprises the nucleotide sequence of nucleotides 700 to 1818 of Seq ID 1.

8. A process for producing a transgenic *Cucur bitacea* plant which is resistant to Squash Mosaic Virus infection comprising the steps of:

a) constructing a recombinant DNA molecule according to claim 1;

b) transforming plant cells with said recombinant DNA; and c) regenerating plants from said transformed plant cells.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 2511 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 1..2370

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| ATG | GAT | TGC | TTC | ACC | TCT | CCT | GAT | AGT | AAT | ATT | TGT | GGT | GGC | ATG | CTG | 48 |
| Met | Asp | Cys | Phe | Thr | Ser | Pro | Asp | Ser | Asn | Ile | Cys | Gly | Gly | Met | Leu | |
| 1 | | | | 5 | | | | | 10 | | | | | 15 | | |
| TTG | GTT | GAT | ACA | GCA | CAT | TTA | AAT | CCG | GAT | AAT | GCT | ATA | AGA | AGC | GTG | 96 |
| Leu | Val | Asp | Thr | Ala | His | Leu | Asn | Pro | Asp | Asn | Ala | Ile | Arg | Ser | Val | |
| | | | 20 | | | | | 25 | | | | | 30 | | | |
| TTC | GTT | GCG | CCA | TTT | ATA | GCT | GGT | GCT | CCT | ATT | CGA | GTT | TTG | CTA | TTT | 144 |
| Phe | Val | Ala | Pro | Phe | Ile | Ala | Gly | Ala | Pro | Ile | Arg | Val | Leu | Leu | Phe | |
| | | 35 | | | | | 40 | | | | | 45 | | | | |
| CCA | GAC | ACC | TTG | GTG | GAG | ATT | GCC | CCG | AAC | ATG | AAC | TCC | CGA | TTC | AAA | 192 |
| Pro | Asp | Thr | Leu | Val | Glu | Ile | Ala | Pro | Asn | Met | Asn | Ser | Arg | Phe | Lys | |
| | 50 | | | | | 55 | | | | | 60 | | | | | |
| TTG | CTA | TGT | ACT | ACG | AGT | AAT | GGC | GAT | GTT | GCA | CCA | GAT | TTC | AAT | TTG | 240 |
| Leu | Leu | Cys | Thr | Thr | Ser | Asn | Gly | Asp | Val | Ala | Pro | Asp | Phe | Asn | Leu | |
| 65 | | | | | 70 | | | | | 75 | | | | | 80 | |
| GCG | ATG | GTC | AAA | GTC | AAC | GTT | GCA | GGT | TGT | GCT | GTT | AGT | TTG | ACT | AAG | 288 |
| Ala | Met | Val | Lys | Val | Asn | Val | Ala | Gly | Cys | Ala | Val | Ser | Leu | Thr | Lys | |
| | | | | 85 | | | | | 90 | | | | | 95 | | |
| ACA | TAC | ACT | CCT | ACA | GCT | TAT | CTC | GAG | CAA | GAG | TTA | ATC | AAA | GAA | AAG | 336 |
| Thr | Tyr | Thr | Pro | Thr | Ala | Tyr | Leu | Glu | Gln | Glu | Leu | Ile | Lys | Glu | Lys | |
| | | | 100 | | | | | 105 | | | | | 110 | | | |
| GGG | GCC | ATT | GTT | CAA | TAT | TTG | AAC | AGG | CAC | ACC | TTC | TCT | ATG | CAT | CGG | 384 |
| Gly | Ala | Ile | Val | Gln | Tyr | Leu | Asn | Arg | His | Thr | Phe | Ser | Met | His | Arg | |
| | | 115 | | | | | 120 | | | | | 125 | | | | |
| AAC | AAT | CAG | ATG | ACA | AAG | GAA | GAG | ATG | CAA | AAG | CAG | CGC | CTA | TCT | TTT | 432 |
| Asn | Asn | Gln | Met | Thr | Lys | Glu | Glu | Met | Gln | Lys | Gln | Arg | Leu | Ser | Phe | |
| | 130 | | | | | 135 | | | | | 140 | | | | | |
| AGG | TTG | GAA | AGT | TGC | TCT | CAC | TTT | GCA | GGA | AAA | GCC | ATC | CTT | CTG | CAC | 480 |
| Arg | Leu | Glu | Ser | Cys | Ser | His | Phe | Ala | Gly | Lys | Ala | Ile | Leu | Leu | His | |
| 145 | | | | | 150 | | | | | 155 | | | | | 160 | |
| GCC | ACT | TTC | TGC | AAA | TCA | ACT | AAC | TTT | GTG | TAC | AAG | ATT | GGT | GGA | GAT | 528 |
| Ala | Thr | Phe | Cys | Lys | Ser | Thr | Asn | Phe | Val | Tyr | Lys | Ile | Gly | Gly | Asp | |
| | | | | 165 | | | | | 170 | | | | | 175 | | |
| GCA | AAA | GAG | GGC | AGC | AAT | GGC | AAT | CTA | ACT | GTC | AAT | GAA | AGC | CAA | TTG | 576 |
| Ala | Lys | Glu | Gly | Ser | Asn | Gly | Asn | Leu | Thr | Val | Asn | Glu | Ser | Gln | Leu | |
| | | | 180 | | | | | 185 | | | | | 190 | | | |
| TCC | TCA | CAC | TCT | CCT | TCT | ACA | CAT | GTT | TTG | CAC | AAG | CAC | AAC | AAC | AGT | 624 |
| Ser | Ser | His | Ser | Pro | Ser | Thr | His | Val | Leu | His | Lys | His | Asn | Asn | Ser | |
| | | 195 | | | | | 200 | | | | | 205 | | | | |
| GGT | GAC | AAT | GAA | GTA | GAG | TTC | TCA | GAA | ATT | GGT | GTA | GTT | GTA | CCA | GGT | 672 |
| Gly | Asp | Asn | Glu | Val | Glu | Phe | Ser | Glu | Ile | Gly | Val | Val | Val | Pro | Gly | |
| | 210 | | | | | 215 | | | | | 220 | | | | | |
| ACT | GGC | AGA | ACC | AAG | GCT | TAT | GGC | CAA | AAT | GAG | CTA | GAT | CTT | GCG | CAA | 720 |
| Thr | Gly | Arg | Thr | Lys | Ala | Tyr | Gly | Gln | Asn | Glu | Leu | Asp | Leu | Ala | Gln | |

|  |  |  |  |  |  |  |  |  |  |  |  |  |  |  |  |  |
|---|---|---|---|---|---|---|---|---|---|---|---|---|---|---|---|---|
| 225 |  |  |  |  | 230 |  |  |  |  | 235 |  |  |  |  | 240 |  |
| CTT | TCT | CTG | GAT | GAC | ACC | AGT | TCT | CTT | CGT | GGA | ACT | GCG | TTG | CAG | ACC | 768 |
| Leu | Ser | Leu | Asp | Asp<br>245 | Thr | Ser | Ser | Leu | Arg<br>250 | Gly | Thr | Ala | Leu | Gln<br>255 | Thr |  |
| AAA | CTG | GCC | ACG | TCC | CGT | ATC | ATT | TTG | AGT | AAG | ACA | ATG | GTC | GGA | AAT | 816 |
| Lys | Leu | Ala | Thr<br>260 | Ser | Arg | Ile | Ile | Leu<br>265 | Ser | Lys | Thr | Met<br>270 | Val | Gly | Asn |  |
| ACT | GTG | CTC | AGG | GAG | GAT | TTG | CTT | GCC | ACC | TTT | TTG | CAA | GAT | AGC | AAT | 864 |
| Thr | Val | Leu<br>275 | Arg | Glu | Asp | Leu | Leu<br>280 | Ala | Thr | Phe | Leu | Gln<br>285 | Asp | Ser | Asn |  |
| GAG | AGG | GCC | GCT | ATA | GAT | TTG | ATT | CGC | ACC | CAT | GTC | ATT | AGA | GGC | AAA | 912 |
| Glu | Arg<br>290 | Ala | Ala | Ile | Asp | Leu<br>295 | Ile | Arg | Thr | His | Val<br>300 | Ile | Arg | Gly | Lys |  |
| ATA | CGC | TGT | GTT | GCT | TCT | ATC | AAT | GTT | CCA | GAA | AAT | ACA | GGT | TGT | GCA | 960 |
| Ile<br>305 | Arg | Cys | Val | Ala | Ser<br>310 | Ile | Asn | Val | Pro | Glu<br>315 | Asn | Thr | Gly | Cys | Ala<br>320 |  |
| TTA | GCT | ATC | TGT | TTC | AAC | AGT | GGC | ATA | ACA | GGA | GCT | GCA | GAT | ACA | GAT | 1008 |
| Leu | Ala | Ile | Cys | Phe<br>325 | Asn | Ser | Gly | Ile | Thr<br>330 | Gly | Ala | Ala | Asp | Thr<br>335 | Asp |  |
| ATT | TAT | ACC | ACA | AGC | TCT | CAG | GAT | GCC | ATT | GTG | TGG | AAT | CCT | GCT | TGC | 1056 |
| Ile | Tyr | Thr | Thr<br>340 | Ser | Ser | Gln | Asp | Ala<br>345 | Ile | Val | Trp | Asn | Pro<br>350 | Ala | Cys |  |
| GAG | AAA | GCT | GTT | GAG | TTG | ACA | TTC | AAC | CCC | AAT | CCT | TGT | GGT | GAT | GCT | 1104 |
| Glu | Lys | Ala<br>355 | Val | Glu | Leu | Thr | Phe<br>360 | Asn | Pro | Asn | Pro | Cys<br>365 | Gly | Asp | Ala |  |
| TGG | AAT | TTT | GTG | TTT | CTG | CAA | CAA | ACA | AAG | GCA | CAT | TTT | GCC | GTT | CAG | 1152 |
| Trp | Asn<br>370 | Phe | Val | Phe | Leu | Gln<br>375 | Gln | Thr | Lys | Ala | His<br>380 | Phe | Ala | Val | Gln |  |
| TGT | GTG | ACC | GGG | TGG | ACT | ACA | ACG | CCA | CTT | ACA | GAT | TTA | GCG | TTG | GTG | 1200 |
| Cys<br>385 | Val | Thr | Gly | Trp | Thr<br>390 | Thr | Thr | Pro | Leu | Thr<br>395 | Asp | Leu | Ala | Leu | Val<br>400 |  |
| CTT | ACA | TGG | CAC | ATT | GAT | AGA | AGC | TTG | TGT | GTG | CCC | AAA | ACT | TTG | ACA | 1248 |
| Leu | Thr | Trp | His | Ile<br>405 | Asp | Arg | Ser | Leu | Cys<br>410 | Val | Pro | Lys | Thr | Leu<br>415 | Thr |  |
| ATT | AGC | TCT | GCA | CAT | GCT | TCT | TTT | CCA | ATA | AAT | CGT | TGG | ATG | GGA | AAG | 1296 |
| Ile | Ser | Ser | Ala<br>420 | His | Ala | Ser | Phe | Pro<br>425 | Ile | Asn | Arg | Trp | Met<br>430 | Gly | Lys |  |
| TTG | GTC | CTT | TCC | GCA | AGG | CCT | GCG | CGT | GTT | CTT | AAG | AGG | ATG | CCC | TTG | 1344 |
| Leu | Val | Leu<br>435 | Ser | Ala | Arg | Pro | Ala<br>440 | Arg | Val | Leu | Lys | Arg<br>445 | Met | Pro | Leu |  |
| GCC | ATT | GGT | GGC | GGG | GCT | GGT | ACC | AAA | GAT | GCT | ATC | TTG | ATG | AAT | ATG | 1392 |
| Ala | Ile<br>450 | Gly | Gly | Gly | Ala | Gly<br>455 | Thr | Lys | Asp | Ala | Ile<br>460 | Leu | Met | Asn | Met |  |
| CCA | AAC | GCT | GTT | ATT | TCA | CTT | CAT | CGA | TAT | TTT | GGA | GGG | GAT | TTT | GTC | 1440 |
| Pro<br>465 | Asn | Ala | Val | Ile | Ser<br>470 | Leu | His | Arg | Tyr | Phe<br>475 | Gly | Gly | Asp | Phe | Val<br>480 |  |
| TTT | GAA | ATA | ACA | AAG | ATG | AGT | TCT | CCT | TAT | ATC | AAG | GCA | ACC | ATT | GCT | 1488 |
| Phe | Glu | Ile | Thr | Lys<br>485 | Met | Ser | Ser | Pro | Tyr<br>490 | Ile | Lys | Ala | Thr | Ile<br>495 | Ala |  |
| TTC | TTT | ATA | GCG | TTT | GGT | GAT | ATT | ACG | GAG | GAA | ATG | ACT | AAC | TTG | GAG | 1536 |
| Phe | Phe | Ile | Ala | Phe<br>500 | Gly | Asp | Ile | Thr | Glu<br>505 | Glu | Met | Thr | Asn | Leu<br>510 | Glu |  |
| AGT | TTT | CCC | CAC | AAG | CTT | GTG | CAG | TTT | CGT | GAA | ATT | CAG | GGG | CGC | ACT | 1584 |
| Ser | Phe | Pro<br>515 | His | Lys | Leu | Val | Gln<br>520 | Phe | Arg | Glu | Ile | Gln<br>525 | Gly | Arg | Thr |  |
| ACC | ATA | ACG | CAC | GCA | AAG | CAA | TTT | TTG | ACG | GCA | TGG | TCT | ACA | CAA | GTA | 1632 |
| Thr | Ile | Thr<br>530 | His | Ala | Lys | Gln | Phe<br>535 | Leu | Thr | Ala | Trp | Ser<br>540 | Thr | Gln | Val |  |
| TTA | AGC | ACT | GTT | AAT | CCT | CAG | AAA | GAT | GGG | TGT | CCC | CAC | TTG | TAT | GCA | 1680 |
| Leu | Ser | Thr | Val | Asn | Pro | Gln | Lys | Asp | Gly | Cys | Pro | His | Leu | Tyr | Ala |  |

| | | | | | | | | | | | | | | | | |
|---|---|---|---|---|---|---|---|---|---|---|---|---|---|---|---|---|
| 545 | | | | | 550 | | | | | 555 | | | | | 560 | |
| CTC | TTG | CAC | GAT | TCT | GCT | ACG | TCA | ACC | ATT | GAA | GGA | AAT | TTT | GTC | ATT | 1728 |
| Leu | Leu | His | Asp | Ser | Ala | Thr | Ser | Thr | Ile | Glu | Gly | Asn | Phe | Val | Ile | |
| | | | | 565 | | | | | 570 | | | | | 575 | | |
| GGT | GTT | AAA | TTG | CTG | GAT | ATT | AGG | AAC | TAT | CGT | GCT | TAC | GGC | CAT | AAC | 1776 |
| Gly | Val | Lys | Leu | Leu | Asp | Ile | Arg | Asn | Tyr | Arg | Ala | Tyr | Gly | His | Asn | |
| | | | 580 | | | | | 585 | | | | | 590 | | | |
| CCT | GGT | TTT | GAG | GGA | CGT | CCG | TTA | CTA | GGA | ATT | TCT | GGG | CAG | AGT | ACC | 1824 |
| Pro | Gly | Phe | Glu | Gly | Arg | Pro | Leu | Leu | Gly | Ile | Ser | Gly | Gln | Ser | Thr | |
| | | 595 | | | | | 600 | | | | | 605 | | | | |
| ATG | GTA | CAG | CAG | CTT | GGA | ACT | TAT | AAT | CCA | ATC | TGG | ATG | GTT | CGC | ACG | 1872 |
| Met | Val | Gln | Gln | Leu | Gly | Thr | Tyr | Asn | Pro | Ile | Trp | Met | Val | Arg | Thr | |
| | 610 | | | | | 615 | | | | | 620 | | | | | |
| CCC | TTA | GAA | AGT | ACA | GCC | CAA | CAG | AAT | TTT | GCG | AGT | TTC | ACT | GCT | GAT | 1920 |
| Pro | Leu | Glu | Ser | Thr | Ala | Gln | Gln | Asn | Phe | Ala | Ser | Phe | Thr | Ala | Asp | |
| 625 | | | | | 630 | | | | | 635 | | | | | 640 | |
| TTG | ATG | GAA | TCC | ACG | ATA | AGT | GGG | GAC | TCT | ACC | GGA | AAT | TGG | AAT | ATC | 1968 |
| Leu | Met | Glu | Ser | Thr | Ile | Ser | Gly | Asp | Ser | Thr | Gly | Asn | Trp | Asn | Ile | |
| | | | | 645 | | | | | 650 | | | | | 655 | | |
| ACA | GTT | TAC | CCG | AGT | CCT | ATA | GCT | AAT | TTA | TTG | AAA | GTG | GCT | GCT | TGG | 2016 |
| Thr | Val | Tyr | Pro | Ser | Pro | Ile | Ala | Asn | Leu | Leu | Lys | Val | Ala | Ala | Trp | |
| | | | 660 | | | | | 665 | | | | | 670 | | | |
| AAG | AAG | GGG | ACT | ATA | AGA | TTT | CAA | CTT | ATT | TGT | CGG | GGT | GCT | GCT | GTT | 2064 |
| Lys | Lys | Gly | Thr | Ile | Arg | Phe | Gln | Leu | Ile | Cys | Arg | Gly | Ala | Ala | Val | |
| | | 675 | | | | | 680 | | | | | 685 | | | | |
| AAG | CAG | TCT | GAC | TGG | GCT | GCG | TCA | CGT | AGA | ATA | GAC | TTG | ATT | AAC | AAC | 2112 |
| Lys | Gln | Ser | Asp | Trp | Ala | Ala | Ser | Arg | Arg | Ile | Asp | Leu | Ile | Asn | Asn | |
| | 690 | | | | | 695 | | | | | 700 | | | | | |
| CTC | TCG | AAC | AAA | GCT | TTA | CCC | GCA | CGT | TCC | TGG | TAT | ATT | ACT | AAG | CCA | 2160 |
| Leu | Ser | Asn | Lys | Ala | Leu | Pro | Ala | Arg | Ser | Trp | Tyr | Ile | Thr | Lys | Pro | |
| 705 | | | | | 710 | | | | | 715 | | | | | 720 | |
| CGA | GGA | GGC | GAC | ATC | GAG | TTT | GAC | TTA | GAG | ATA | GCG | GGA | CCA | AAC | AAT | 2208 |
| Arg | Gly | Gly | Asp | Ile | Glu | Phe | Asp | Leu | Glu | Ile | Ala | Gly | Pro | Asn | Asn | |
| | | | | 725 | | | | | 730 | | | | | 735 | | |
| GGT | TTC | GAA | ATG | GCG | AAC | TCC | AGT | TGG | GCT | TTC | CAG | ACC | ACA | TGG | TAT | 2256 |
| Gly | Phe | Glu | Met | Ala | Asn | Ser | Ser | Trp | Ala | Phe | Gln | Thr | Thr | Trp | Tyr | |
| | | | 740 | | | | | 745 | | | | | 750 | | | |
| TTG | GAA | ATT | GCC | ATA | GAC | AAT | CCT | AAG | CAA | TTC | ACT | CTT | TTT | GAG | TTA | 2304 |
| Leu | Glu | Ile | Ala | Ile | Asp | Asn | Pro | Lys | Gln | Phe | Thr | Leu | Phe | Glu | Leu | |
| | | 755 | | | | | 760 | | | | | 765 | | | | |
| AAT | GCT | TGT | CTT | ATG | GAA | GAC | TTT | GAA | GTG | GCT | GGA | AAT | ACT | TTA | AAT | 2352 |
| Asn | Ala | Cys | Leu | Met | Glu | Asp | Phe | Glu | Val | Ala | Gly | Asn | Thr | Leu | Asn | |
| | 770 | | | | | 775 | | | | | 780 | | | | | |
| CCA | CCT | ATT | TTG | CTT | TCA | TAGTTGTTTC | GTTGTTTGTT | TCCTTCTTTT | | | | | | | | 2400 |
| Pro | Pro | Ile | Leu | Leu | Ser | | | | | | | | | | | |
| 785 | | | | | 790 | | | | | | | | | | | |

CTGGGTTTTG TTGTGGCTTC TTTCCCAGTT CGCTTTAGAA GCCTCTCTTT GTAAATTTTA 2460

AGAGCTTGTT TTCTTTGATG CATTCTCTTT TCTTTTTAAA AAAAAAAAA A 2511

( 2 ) INFORMATION FOR SEQ ID NO:2:

( i ) SEQUENCE CHARACTERISTICS:
           ( A ) LENGTH: 790 amino acids
           ( B ) TYPE: amino acid
           ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Asp | Cys | Phe | Thr | Ser | Pro | Asp | Ser | Asn | Ile | Cys | Gly | Gly | Met | Leu |
| 1 | | | | 5 | | | | | 10 | | | | | 15 | |

| | | | | | | | | | | | | | | |
|---|---|---|---|---|---|---|---|---|---|---|---|---|---|---|
| Leu | Val | Asp | Thr | Ala | His | Leu | Asn | Pro | Asp | Asn | Ala | Ile | Arg | Ser | Val |
| | | | 20 | | | | | 25 | | | | 30 | | |
| Phe | Val | Ala | Pro | Phe | Ile | Ala | Gly | Ala | Pro | Ile | Arg | Val | Leu | Leu | Phe |
| | | 35 | | | | 40 | | | | | 45 | | | |
| Pro | Asp | Thr | Leu | Val | Glu | Ile | Ala | Pro | Asn | Met | Asn | Ser | Arg | Phe | Lys |
| | 50 | | | | 55 | | | | | 60 | | | | |
| Leu | Leu | Cys | Thr | Thr | Ser | Asn | Gly | Asp | Val | Ala | Pro | Asp | Phe | Asn | Leu |
| 65 | | | | 70 | | | | 75 | | | | | 80 |
| Ala | Met | Val | Lys | Val | Asn | Val | Ala | Gly | Cys | Ala | Val | Ser | Leu | Thr | Lys |
| | | | 85 | | | | 90 | | | | 95 | |
| Thr | Tyr | Thr | Pro | Thr | Ala | Tyr | Leu | Glu | Gln | Glu | Leu | Ile | Lys | Glu | Lys |
| | | | 100 | | | | 105 | | | | 110 | |
| Gly | Ala | Ile | Val | Gln | Tyr | Leu | Asn | Arg | His | Thr | Phe | Ser | Met | His | Arg |
| | | 115 | | | | 120 | | | | 125 | | |
| Asn | Asn | Gln | Met | Thr | Lys | Glu | Glu | Met | Gln | Lys | Gln | Arg | Leu | Ser | Phe |
| 130 | | | | 135 | | | | 140 | | | | |
| Arg | Leu | Glu | Ser | Cys | Ser | His | Phe | Ala | Gly | Lys | Ala | Ile | Leu | Leu | His |
| 145 | | | 150 | | | | 155 | | | | 160 |
| Ala | Thr | Phe | Cys | Lys | Ser | Thr | Asn | Phe | Val | Tyr | Lys | Ile | Gly | Gly | Asp |
| | | | 165 | | | 170 | | | | 175 | |
| Ala | Lys | Glu | Gly | Ser | Asn | Gly | Asn | Leu | Thr | Val | Asn | Glu | Ser | Gln | Leu |
| | | | 180 | | | | 185 | | | | 190 | |
| Ser | Ser | His | Ser | Pro | Ser | Thr | His | Val | Leu | His | Lys | His | Asn | Asn | Ser |
| | | 195 | | | | 200 | | | | 205 | | |
| Gly | Asp | Asn | Glu | Val | Glu | Phe | Ser | Glu | Ile | Gly | Val | Val | Pro | Gly |
| | 210 | | | | 215 | | | | 220 | | | |
| Thr | Gly | Arg | Thr | Lys | Ala | Tyr | Gly | Gln | Asn | Glu | Leu | Asp | Leu | Ala | Gln |
| 225 | | | | 230 | | | | 235 | | | | 240 |
| Leu | Ser | Leu | Asp | Asp | Thr | Ser | Ser | Leu | Arg | Gly | Thr | Ala | Leu | Gln | Thr |
| | | | 245 | | | | 250 | | | | 255 |
| Lys | Leu | Ala | Thr | Ser | Arg | Ile | Ile | Leu | Ser | Lys | Thr | Met | Val | Gly | Asn |
| | | | 260 | | | | 265 | | | | 270 | |
| Thr | Val | Leu | Arg | Glu | Asp | Leu | Leu | Ala | Thr | Phe | Leu | Gln | Asp | Ser | Asn |
| | | 275 | | | | 280 | | | | 285 | | |
| Glu | Arg | Ala | Ala | Ile | Asp | Leu | Ile | Arg | Thr | His | Val | Ile | Arg | Gly | Lys |
| | 290 | | | | 295 | | | | 300 | | | |
| Ile | Arg | Cys | Val | Ala | Ser | Ile | Asn | Val | Pro | Glu | Asn | Thr | Gly | Cys | Ala |
| 305 | | | | 310 | | | | 315 | | | | 320 |
| Leu | Ala | Ile | Cys | Phe | Asn | Ser | Gly | Ile | Thr | Gly | Ala | Ala | Asp | Thr | Asp |
| | | | 325 | | | | 330 | | | | 335 |
| Ile | Tyr | Thr | Thr | Ser | Ser | Gln | Asp | Ala | Ile | Val | Trp | Asn | Pro | Ala | Cys |
| | | | 340 | | | | 345 | | | | 350 | |
| Glu | Lys | Ala | Val | Glu | Leu | Thr | Phe | Asn | Pro | Asn | Pro | Cys | Gly | Asp | Ala |
| | | 355 | | | | 360 | | | | 365 | | |
| Trp | Asn | Phe | Val | Phe | Leu | Gln | Gln | Thr | Lys | Ala | His | Phe | Ala | Val | Gln |
| | 370 | | | | 375 | | | | 380 | | | |
| Cys | Val | Thr | Gly | Trp | Thr | Thr | Pro | Leu | Thr | Asp | Leu | Ala | Leu | Val |
| 385 | | | | 390 | | | | 395 | | | | 400 |
| Leu | Thr | Trp | His | Ile | Asp | Arg | Ser | Leu | Cys | Val | Pro | Lys | Thr | Leu | Thr |
| | | | 405 | | | | 410 | | | | 415 |
| Ile | Ser | Ser | Ala | His | Ala | Ser | Phe | Pro | Ile | Asn | Arg | Trp | Met | Gly | Lys |
| | | | 420 | | | 425 | | | | 430 | | |
| Leu | Val | Leu | Ser | Ala | Arg | Pro | Ala | Arg | Val | Leu | Lys | Arg | Met | Pro | Leu |

```
                         435                           440                          445
Ala    Ile    Gly    Gly    Gly    Ala    Gly    Thr    Lys    Asp    Ala    Ile    Leu    Met    Asn    Met
       450                           455                         460

Pro    Asn    Ala    Val    Ile    Ser    Leu    His    Arg    Tyr    Phe    Gly    Gly    Asp    Phe    Val
465                          470                           475                                           480

Phe    Glu    Ile    Thr    Lys    Met    Ser    Ser    Pro    Tyr    Ile    Lys    Ala    Thr    Ile    Ala
                            485                           490                                 495

Phe    Phe    Ile    Ala    Phe    Gly    Asp    Ile    Thr    Glu    Glu    Met    Thr    Asn    Leu    Glu
                     500                           505                                 510

Ser    Phe    Pro    His    Lys    Leu    Val    Gln    Phe    Arg    Glu    Ile    Gln    Gly    Arg    Thr
              515                           520                           525

Thr    Ile    Thr    His    Ala    Lys    Gln    Phe    Leu    Thr    Ala    Trp    Ser    Thr    Gln    Val
       530                           535                           540

Leu    Ser    Thr    Val    Asn    Pro    Gln    Lys    Asp    Gly    Cys    Pro    His    Leu    Tyr    Ala
545                                 550                           555                                    560

Leu    Leu    His    Asp    Ser    Ala    Thr    Ser    Thr    Ile    Glu    Gly    Asn    Phe    Val    Ile
                            565                           570                                 575

Gly    Val    Lys    Leu    Leu    Asp    Ile    Arg    Asn    Tyr    Arg    Ala    Tyr    Gly    His    Asn
                     580                           585                                 590

Pro    Gly    Phe    Glu    Gly    Arg    Pro    Leu    Leu    Gly    Ile    Ser    Gly    Gln    Ser    Thr
              595                           600                                 605

Met    Val    Gln    Gln    Leu    Gly    Thr    Tyr    Asn    Pro    Ile    Trp    Met    Val    Arg    Thr
       610                           615                           620

Pro    Leu    Glu    Ser    Thr    Ala    Gln    Gln    Asn    Phe    Ala    Ser    Phe    Thr    Ala    Asp
625                                 630                           635                                    640

Leu    Met    Glu    Ser    Thr    Ile    Ser    Gly    Asp    Ser    Thr    Gly    Asn    Trp    Asn    Ile
                            645                           650                                 655

Thr    Val    Tyr    Pro    Ser    Pro    Ile    Ala    Asn    Leu    Leu    Lys    Val    Ala    Ala    Trp
                     660                           665                                 670

Lys    Lys    Gly    Thr    Ile    Arg    Phe    Gln    Leu    Ile    Cys    Arg    Gly    Ala    Ala    Val
              675                           680                                 685

Lys    Gln    Ser    Asp    Trp    Ala    Ala    Ser    Arg    Arg    Ile    Asp    Leu    Ile    Asn    Asn
       690                           695                           700

Leu    Ser    Asn    Lys    Ala    Leu    Pro    Ala    Arg    Ser    Trp    Tyr    Ile    Thr    Lys    Pro
705                                 710                           715                                    720

Arg    Gly    Gly    Asp    Ile    Glu    Phe    Asp    Leu    Glu    Ile    Ala    Gly    Pro    Asn    Asn
                            725                           730                                 735

Gly    Phe    Glu    Met    Ala    Asn    Ser    Ser    Trp    Ala    Phe    Gln    Thr    Thr    Trp    Tyr
                     740                           745                                 750

Leu    Glu    Ile    Ala    Ile    Asp    Asn    Pro    Lys    Gln    Phe    Thr    Leu    Phe    Glu    Leu
              755                           760                                 765

Asn    Ala    Cys    Leu    Met    Glu    Asp    Phe    Glu    Val    Ala    Gly    Asn    Thr    Leu    Asn
       770                           775                           780

Pro    Pro    Ile    Leu    Leu    Ser
785                                 790
```

( 2 ) INFORMATION FOR SEQ ID NO:3:

( i ) SEQUENCE CHARACTERISTICS:
           ( A ) LENGTH: 35 base pairs
           ( B ) TYPE: nucleic acid
           ( C ) STRANDEDNESS: single
           ( D ) TOPOLOGY: linear ( i i ) MOLECULE TYPE: cDNA ( x i ) SEQUENCE DESCRIPTION: SEQ ID NO:3:

TCTTGAGGAT CCATGGGAAC TGGGAAAGAA GCCAC                                        35

( 2 ) INFORMATION FOR SEQ ID NO:4:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

TACTTATCTA GAACCATGGA GCTAGATCTT GCGCAACT                                     38

( 2 ) INFORMATION FOR SEQ ID NO:5:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

TACAGTGGAT CCATGGTTCT ACTGCCCAGA AATTCCTAGT A                                 41

( 2 ) INFORMATION FOR SEQ ID NO:6:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

TACAGTTCTA GAAGAACCAT GGTACAGCAG C                                            31